United States Patent
Schürenberg et al.

(10) Patent No.: US 7,399,640 B2
(45) Date of Patent: Jul. 15, 2008

(54) STRUCTURED BIOSAMPLE SUPPORT PLATES FOR MASS SPECTROSCOPIC ANALYSES AND PROCEDURES FOR USE

(75) Inventors: Martin Schürenberg, Tarmstedt (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 792 days.

(21) Appl. No.: 10/828,153

(22) Filed: Apr. 20, 2004

(65) Prior Publication Data

US 2004/0197921 A1    Oct. 7, 2004

Related U.S. Application Data

(62) Division of application No. 09/943,076, filed on Aug. 30, 2001, now abandoned.

(51) Int. Cl.
*G01N 24/00* (2006.01)
*B01J 19/08* (2006.01)
*H01J 49/40* (2006.01)

(52) U.S. Cl. .................. 436/173; 422/186; 422/186.05; 250/288

(58) Field of Classification Search ........................ None
See application file for complete search history.

(56) References Cited

U.S. PATENT DOCUMENTS

2003/0106997 A1*  6/2003  Beecher et al. ............. 250/288

OTHER PUBLICATIONS

Brockman et al. "Probe-immobilized affinity chromatography/mass spectrometry", Anal. Chem., 1995, v. 67, pp. 4581-4585.*
Liang et al. "on-probe immunoaffinity extraction by matrix-assisted laser desorption /ionization mass spectrometry", Anal. Chem., 1998, v. 70, pp. 498-503.*

* cited by examiner

*Primary Examiner*—Yelena G Gakh
(74) *Attorney, Agent, or Firm*—Law Offices of Paul E. Kudirka

(57) ABSTRACT

The invention relates to sample support plates with hydrophilic anchors in a strongly hydrophobic environment for mass spectroscopic analysis of biosubstances with ionization by matrix-assisted laser desorption and ionization (MALDI), procedures for manufacturing these sample supports, and connected procedures for loading these sample supports with biomolecular samples. The invention provides areas with affinity adsorbents adjacent to the hydrophilic anchors for purifying biosubstances and, if wanted, for performing an affinity selection of biosubstances, whereby the finally prepared matrix sample crystals with the biosubstances for the MALDI analysis are well localized on the hydrophilic anchors.

6 Claims, 1 Drawing Sheet

STRUCTURED BIOSAMPLE SUPPORT PLATES FOR MASS SPECTROSCOPIC ANALYSES AND PROCEDURES FOR USE

CROSS-REFERENCE TO RELATED APPLICATONS

This application is a divisional of U.S. patent application Ser. No. 09/943,076, filed Aug. 30, 2001 now abandoned.

BACKGROUND OF THE INVENTION

Mass spectrometry involving ionization by matrix-assisted laser desorption (MALDI) has established itself as a standard procedure for the analysis of biosubstances with large molecules. For this purpose, time-of-flight mass spectrometers (TOF-MS) are usually employed, although Fourier transform ion cyclotron resonance spectrometers (FT-ICR) or radio frequency quadrupole ion trap mass spectrometers (in short: ion traps) have also been utilized.

In the following, the molecules of biosubstances to be studied will be referred to simply as "analyte molecules" or "biomolecules". In all cases, analyte molecules are present either in very diluted form in aqueous solutions, pure or mixed with organic solvents. Sometimes these analytical solutions are very complex and dirty with respect to the requirements of the analytical procedures, e.g., in the case of body fluids.

The biosubstances include all biopolymers and sometimes other substances with large molecules such as corticosteroids. "Biopolymers" comprise oligonucleotides (i.e. fragments of genetic material in various forms such as DNA or RNA), polysaccharides and proteins (the essential building blocks of the living world) as well as their special analogues and conjugates such as glycoproteins or lipoproteins, and peptides arising from the action of digestive enzymes.

The selection of matrix substance for MALDI depends on the type of analyte molecule; more than a hundred different matrix substances are now known. One of the tasks of the matrix substances is to isolate the analyte molecules from each other wherever possible and bind them to the sample support, to transfer the molecules into the vapor phase by forming a vapor cloud during the laser bombardment, and ultimately to ionize the biomolecules by protonation or deprotonation. For this task it has proven useful to incorporate the analyte molecules individually in the crystals of the matrix substances during their crystallization, or at least finely distributed in the boundary areas between the crystals. Here it seems important to separate the analyte molecules from each other, i.e., no clusters of analyte molecules should be allowed in the prepared matrix crystal sample.

A variety of procedures are known for applying analytes and matrices. The simplest of these entails the pipetting of a solution containing analyte and matrix onto a cleaned, metallic sample support. The drop of solution wets a certain area of the metal surface (or its oxide layer) whose size on hydrophilic surfaces is many times larger than that of the diameter of a drop. The size depends on the hydrophilicity and the microstructuring of the metal surface as well as on the properties of the droplet, in particular that of the solvent. After drying of the solution, a sample spot consisting of small matrix crystals forms that is the same size as that of the originally wetted surface area. The matrix crystals are usually not uniformly distributed throughout the formerly wetted area. As a rule, crystals of the matrix start growing at the inner margin of the wetting surface on the metal plate. They then grow towards the interior of the wetting surface. They often form thin needle crystals, as is the case for example for the frequently used matrices 5-dihydroxybenzoic acid (DHB) or 3-hydroxypicolinic acid (HPA), which often stand out from the carrier plate at the interior of the spot. The center of the spot is frequently empty or covered with fine crystals, although often they cannot be used for MALDI ionization because of their high concentration of alkaline salts. The loading of the crystals with biomolecules is also very uneven. This type of loading therefore requires viewing of the sample support surface during MALDI ionization by a video microscope which can be found in any commercially available mass spectrometer used for this type of analysis. Ion yield and mass resolution vary in the sample spot from place to place. It is often an arduous process to find a suitable position on the sample spot with a satisfactory analyte ion yield and mass resolution, and only experience, trial and error allow for improvements.

Although there are control programs for mass spectrometers with algorithms for automatically seeking the best spots for MALDI-ionization, such procedures, involving many attempts and evaluations, are necessarily very slow.

With other loading procedures the matrix substance is already present on the carrier plate before application of the solvent droplets, which now only contain analyte molecules.

If the surface of the sample carrier plate is not hydrophilic, but hydrophobic, smaller crystal conglomerates are formed, but the droplets tend to wander in an uncontrollable manner during drying. Hence the localization of the crystal conglomerates cannot be predicted and must be sought during the MALDI process. Furthermore, there is a considerable risk that droplets will conglomerate and thus render a separate analysis of samples impossible.

Biosample analyses are now performed in their thousands, a situation which demands automatic high throughput procedures. A visual control or search, or even an automated search, would obstruct such a high throughput procedure.

A procedure has now been developed by the applicant which leads to local and size-defined crystallization fields on small hydrophilic anchor regions of 100 to 800 micrometer in diameter within an otherwise hydrophobic surface (DE 197 54 978 C2). The aqueous drops are fixed by the hydrophilic anchors and prevented from wandering even when they initially rest on surrounding lyophobic areas due to their weight. During drying the droplets withdraw onto the anchor, and relatively dense, homogeneously distributed, crystalline conglomerates arise on the exact position of these anchors (sometimes even structured as a single compact crystalline block depending on the type and concentration of matrix substance). It could be shown that the detection limit for analyte molecules improves with reduction of the surface area of the wetting surface. Thus, smaller quantities of analytes and more diluted solutions can be worked with during sample preparation; such an advantage is expressed in better running biochemical preparatory procedures and reductions in chemical material costs. With a suitable preparation the analytical sensitivity over the surface of the sample is highly uniform. Thus the ionization process can be freed from the need to perform visual or automated searches for favorable sites; instead a "blind" bombardment of the crystal conglomerates with desorbing laser light can be used. This preparation method for prelocated spots of equal sensitivity accelerates the analytical process.

The crystal conglomerates forming on the hydrophilic anchor surfaces reveal a microcrystalline structure suitable for the MALDI-process. As the speed of the drying process is increased, the crystalline structure becomes finer.

Here a "hydrophobic" surface is understood as a water repellant surface, i.e. one resistant to wetting by aqueous solutions. Correspondingly, a "hydrophilic" surface is understood as one that can be easily wetted by water. "Oleophobic" and "oleophilic" (also referred to sometimes as "lipophobic" and "lipophilic") refer to surfaces which repel or which can be wetted by oil, respectively. Organic solvents that are not miscible with water usually have an oily nature in this meaning of wettability, i.e. they can wet oleophilic faces. They are as a rule miscible with oil. Organic solvents that are miscible with water, e.g. methanol, acetone or acetonitrile, can wet both oleophilic and hydrophilic surfaces in a pure state. However, the wettability of oleophilic surfaces reduces as the water content increases.

An opinion persisted for a long time that hydrophobic surfaces are always also oleophilic, and that oleophobic surfaces are always hydrophilic. However, for some years it has been known that surfaces exist which are both hydrophobic and oleophobic; these include smooth surfaces of perfluorinated hydrocarbons such as polytetrafluoroethylene (PTFE). Such surfaces are designated here as "lyophobic", a term which has been adopted from colloidal science.

Recently, it has also become known that the wetting or liquid repelling character of a surface strongly depends on its microstructure. An example of this is the so called "lotus effect" (named after the lotus-plant).

The hydrophobicity (oleophobicity, lyophobicity) can be measured essentially by measuring the contact angle which the liquid develops under standardized conditions at the edge of the wetting surface with the solid surface. In an absolute sense a surface of a material is referred to as hydrophobic, oleophobic or lyophobic if the contact angle of the respective liquid level in a capillary constructed from this material is more than 90°. Such a definition is hard to apply to the contact angle of a droplet sitting on a flat surface since the droplet size actually plays a bigger role in this case. In the following, the terms hydrophile and hydrophobic are not used in an absolute, but rather a relative sense: a surface is more hydrophobic towards a liquid than another surface if the contact angle is larger. In general, a surface is already regarded as hydrophobic if the contact angle is smaller than 90°, but a drop does not run on the surface to form a large wetting surface.

A surface is particularly designated as "hydrophobic" when a drop retracts on a surface during drying or aspiration with a pipette, reducing the wetted surface reduces in size and leaving behind a dry surface (so called "dynamic hydrophobia").

As a rule, biomolecules are best dissolved in water, sometimes with the addition of organic, water-soluble solvents such as alcohols, acetone or acetonitrile. The analytical solutions of biomolecules sometimes also contain other substances such as glycols, glue-like buffering agents, salts, acids or bases depending on their preparation. The MALDI process is disrupted considerably by the presence of these impurities, sometimes through prevention of protonation, and sometimes through the formation of adducts. In particular, alkali ions often form adducts with analyte molecules of varying size and prevent any precise mass determination. The concentration of alkali ions in the sample preparation, as well as the concentration of other impurity substances must be kept extremely low by careful purification procedures.

For purification and simultaneous enrichment of biomolecules one can use so-called affinity adsorption media similar to those used in affinity chromatography. While in affinity chromatography one uses highly bioselective affinity adsorbents, for the purification of initially unknown mixtures of biopolymers without losses of special types of biomolecules one needs non-specific adsorbents that can bind all biomolecular constituents of the mixture to as near a similar degree as possible.

For purification of peptides, proteins or DNA mixtures, sponge-like microspheres of adsorbent material (such as POROS, a registered trademark of Perseptive Biosystems, Inc.), pipette tips filled with sponge-like adsorbent (such as ZIPTIPs, a registered trademark of Millipore Corporation) or C18 coated magnetized spheres (such as GenoPure, a product of Bruker Daltonics, Inc.) have proven particularly useful until now. These materials are all strongly oleophilic and bind peptides or oligonucleotides via hydrophobic bonds. As a rule, biomolecules can be eluted using aqueous methanol or acetonitrile solutions, and elution can often be assisted by altering the pH-value. However, purification with these materials is labor-intensive since it requires additional materials and additional procedural steps.

Affinity capture methods have become known also for biospecific selection of certain biomolecules in connection with mass spectrometric analysis, see e.g., U.S. Pat. No. 6,020,208, U.S. Pat. No. 6,027,942, or U.S. Pat. No. 5,894, 063 (T. W. Hutchens and T.-T. Yip). Such biospecific affinity adsorption processes can be likewise used for purification.

As an alternative or additional procedure one can also remove noxious cations by substitution with ion exchangers. A procedure has also been developed by us to accomplish this (DE 199 23 761 C2).

SUMMARY OF THE INVENTION

The basic idea of the invention is to equip the surface of a strongly hydrophobic sample support plate with small, contingent, hydrophilic areas serving as anchors for sample droplets (as has already been methodically developed to the production stage by the applicant), but to apply affinity adsorbents (e.g. biospecific affinity chromatographic phases) to areas adjacent to the hydrophilic anchors. The areas with affinity adsorbents are usually less hydrophobic than the lyophobic surface of the sample carrier, but much more hydrophobic than the hydrophilic anchor areas. Such adsorbents should bind predetermined kinds of biosubstances from aqueous solutions and re-release them into solution upon wetting by so-called elution media or eluants.

The hydrophilic anchor regions are chosen to be so small that when the sample is loaded in the form of not too small drops, the area covered by the sample droplet overlaps with the affinity region. The biomolecules are then bound in these regions by affinity adsorption. In this bound state the biomolecules can then be washed with non-eluting liquids.

Such a zone with affinity adsorbents favorably forms a ring around the hydrophilic anchor, and the strongly hydrophobic surface region of the sample carrier plate surrounds this ring area.

Although the eluant is usually a mixture of a large part of organic solvent with a smaller part of water, it can have a very different composition, as is the case when elution is controlled by the pH value. For the MALDI sample preparation the eluant solution also should be able to solve the MALDI matrix substance. The matrix substance can be already contained within the eluant solution when it is loaded on the sample carrier plate, or the matrix can be loaded in an extra step to the anchors before the eluant solution is loaded. In the latter case, some matrix substance is solved again in the eluant solution. The eluant fluid droplets wet the affinity area so that the biomolecules are desorbed and solved again. During drying of the eluant solution, the droplets retract more and more from the affinity adsorbents towards the hydrophilic anchor areas, leaving behind the dry affinity adsorbent area, and a large part of the biomolecules is incorporated into the matrix crystals forming on the hydrophilic anchor surfaces.

Depending on the analytical task, the affinity adsorbents can act very bioselectively towards relatively few types of biosubstances, or very non-selectively towards a much wider range of biosubstances. Non-selective affinity adsorbents are particularly suitable for the purification of peptide or oligonucleotide mixtures; these act via relatively non-selective hydrophobic bonds.

As example for a non-selective, hydrophobic binding of peptides, proteins or oligonucleotides, surface bound alkane chains varying in size between 4 and 18 carbon atoms (or even longer) can be used, so-called C4 to C18 coatings. The alkane chains can be covalently bonded via, e.g., sulphur bridges directly to metal surfaces. As examples for extremely bioselective affinity adsorbents, coatings with antibodies can be used that are bound in a known way to a specially prepared molecular layer which in turn is covalently bonded to the plate surface. For oligonucleotides, coatings with biotinylated counterstrands can for example be used which are easily bound to surface-bound strepatividin via strepatividin-biotin bonds. Here the biotin-streptavidin bond can even be reversed so that the strepatividin layer can then be coated with other counterstrands.

A surface of only one square millimeter suffices in order to bind several picomoles of analyte substances. A coating density then arises which corresponds to only a tiny fraction of a monomolecular layer. However, MALDI analysis can already be performed with merely a femtomole of each of the substances present.

For special analytical procedures several affinity adsorbents with different bioselectivity, each surrounding its own hydrophilic anchor, can be coated on a single carrier plate. A small carrier plate of this type with about 4 to 10 affinity adsorbents may be exposed in total to a mixture of biomolecules in a sample fluid to measure a certain biomolecule profile of this sample.

The anchor surfaces can additionally be coated with cation exchanging (and therefore permanently hydrophilic) materials so that even the last cation residues can be removed.

With careful cleaning, the sample carrier plates can be reused many times. The number of applications depends most of all upon contamination by usually high-molecular-weight, strongly hydrophobic substances which can no longer be washed away from the affinity adsorbent regions and may change the affinity characteristic.

Figure 1A:
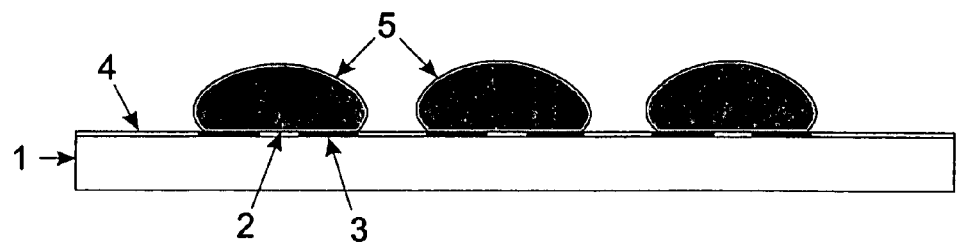
FIG. 1A shows a metallic sample carrier plate (1) with hydrophilic anchors (2) and surrounding affinity regions (3) in strongly hydrophobic surroundings (4), with pipette-applied sample droplets (5) that cover large areas of the affinity regions by deforming under their own weight so that the biomolecules are affinely bound there. For non-sective washing the affinity regions can be coated with C18. The hydrophilic anchors may be formed by the bare metal surface; organic-inorganic nanocomposite materials with about 4 micrometers thickness may form the strongly hydrophobic layer around the affinity regions.
Figure 1B:
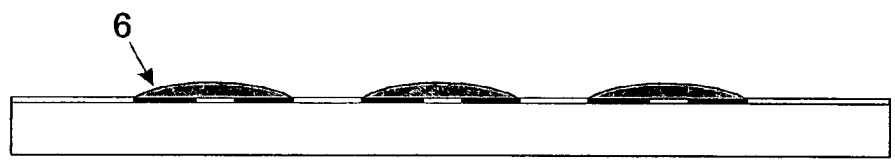
FIG. 1B shows the same sample carrier plate after washing, drying, and application of the much smaller eluant fluid droplets (6) that wet the affinity region and resolubilize the biomolecules. Hereby, the eluant fluid might consist e.g. of 95% acetonitrile with 5% water, in which about 0.5% matrix substance is dissolved.
Figure 1C:

Eluant fluid droplets (7) during drying are represented in FIG. 1C. Since acetonitrile is essentially the only substance to evaporate initially, the mixture in which the matrix substance is dissolved now consists of about 50% acetonitrile and 50% water when the volume is reduced to 10% of the initially pipetted volume. This solution still acts as an eluant containing solved biomolecules, although it is already retracting from the affinity regions.

Figure 1D:
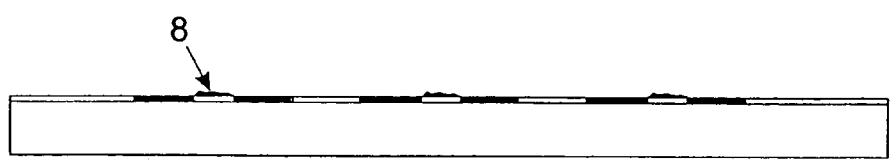

FIG. 1D depicts the matrix crystal conglomerates (8) on the hydrophilic anchors after complete drying of the eluant. The biomolecules are now found mainly within the crystal conglomerates.

DETAILED DESCRIPTION

The convenient preparation of biosample supports with purification properties shall be described at first together with their form. Following this, corresponding purifying loading procedures will be described.

Well-cleaned, fat-free surfaces used for metallic sample carriers in MALDI are as a rule sufficiently hydrophilic by nature towards the aqueous sample solutions; a sample droplet usually widens to a spot size corresponding to several droplet diameters. The hydrophilicity is produced by the hydroxyl groups at the metal surface which form as a result of the action of moist air on any metal (even on noble metals).

In order to facilitate production, it is entirely appropriate for this invention to utilize sample supports constructed from metal or metal coated plastics, and also not to apply any further coating to these metal surfaces as hydrophilic anchor surfaces. The metallic basis determines the acceleration potential for the ions produced by the ensuing MALDI process. Special alloy high-grade stainless steels have proven especially suitable, although the same can be said of pure nickel surfaces. For this reason sample support plates, e.g. based on nickel-plated diecasting aluminum, can be constructed.

The surface of the sample supports external to both the hydrophilic anchors and the areas which will later be coated with affinity adsorbents must now be made lyophobic.

Recently a number of procedures have been developed for producing lyophobic surfaces. Apart from the already known coating with perfluorinated substances such as PTFE (for example with TEFLON, a registered trademark of E. I. DuPont De Nemours and Company Corporation), coating with organic-inorganic sol gel nanocomposite materials represents a favorable alternative (DE 41 18 184), see for example R. Kasemann, H. Schmidt, S. Brück, Bol. Soc. Esp. Ceram. Vid. 31-6, Vol. 7, (1992), 75. The nanocomposite materials can be burned into metals, glass or plastics as layers which are only a few microns thick, very smooth and scratch-resistant. Layering with PTFE is usually not as thin and smooth as with nanocomposite materials, and in general is less usable since it is usually several hundred microns thick and tends to produce strong electrical surface charging during MALDI ionization which has negative effects on the mass spectra produced.

The areas becoming subsequently the anchor and affinity surfaces, can be protected initially with resoluble protective lacquers using a special imprinting procedure, for example by imprinting round spots with a diameter of about 1.4 mm. After spraying and burning in the nanocomposite solution, the soluble lacquers are removed, re-exposing the imprinted areas. The spots of protective lacquer determine the external diameters of the affinity rings. Diameters of about 0.8 to about 2 mm have proven suitable, with diameters of between 1.2 and 1.5 mm being particularly favorable because droplets of about 2 microliter just cover this area.

In a second imprinting procedure the areas becoming subsequently the hydrophilic anchor fields are imprinted with soluble protective lacquer, for example as round spots of 0.4 mm diameter sitting in the center of the subsequent affinity area. The protective lacquer can be applied in the form of minute droplets, for example, using a printing device of the kind used in ink jet printers, although silk-screen (or mesh-screen) printing procedures have also proven suitable. With both procedures, a good positioning accuracy of lacquering is attainable. A good positioning accuracy is needed for the subsequent automatic MALDI-analysis procedure.

The hydrophilic anchor surfaces should ideally have diameters of between 100 and 800 micrometers, with those of 200, 400 and 600 micrometer in diameter having proven particularly favorable for a number of applications.

The next stage is that the rings around these anchor regions imprinted with protective lacquer are coated with affinity adsorbents. The coating techniques are well known in principle to experts in chromatography. With C18 alkane coating, the non-coated metal surface around the subsequent anchor regions can be covered by a self-organizing coating liquid using an aqueous solution of alkanthioates. Hereby, the alkane chains automatically bond directly to the metal surface covalently in a known manner via terminal sulphur bridges. This covalent bonding is highly stable. A particularly effective bonding is achieved when the surfaces are first electrolytically gold-plated. However, other coating procedures involving alkane chains also exist, such as those involving electrical plasma.

The dissolution of protective lacquer spots on the anchor regions completes the preparation of the biosample carrier plates with selection and cleaning functionality. These sample supports now have central, metallic, hydrophilic anchors, each with a diameter of e.g. 0.4 mm, around which there are ring-shaped areas with affinity adsorbents. These areas may be coated with C18, for example, for a selection-free purification of peptide mixtures, and can have an external diameter of about 1.4 mm.

In a further development of the invention the hydrophilic anchor regions can also be coated with ion exchanging layers. NAFION (a registered trademark of E. I. DuPont De Nemours and Company Corporation), for example, can be applied as a solution. The solution forms small droplets on the hydrophilic anchors which leave behind a NAFION film after evaporation of the solvent. A solution of adhesive can also be applied, which can be completely dusted over with a powder of ion exchanger material after almost complete drying. If a powder with particles of about 5 to 20 microns in diameter is employed (mesh 1000), a highly regular coating results after firm pressing, drying and vigorous washing; this has a high capacity to absorb alkali ions. It is also possible to polymerize the materials directly onto the hydrophilic anchor surface. Here as well, the hydrophilicity of the anchor surfaces facilitates a uniform application. Ion exchangers are always extremely hydrophilic by nature so that the anchor surfaces remain hydrophilic even after coating with ion exchangers.

The sample droplets are usually applied with pipettes onto the hydrophilic anchor regions of the MALDI biosample supports. Multiple pipettes are employed for the simultaneous application of many sample droplets from microtitration plates; pipette robots in pipette machines apply such multi-head pipettes (see for example DE 196 28 178).

It is therefore particularly favorable to use sample supports of the same dimensions as microtiter plates and to adapt the array of the hydrophilic anchor regions to that of the microtiter plates. It is also favorable if the sample supports have the same form as a microtiter plate, since they can then be processed and transported using standard pipette robots. Since a higher sample density can be achieved on the sample support than is possible with most microtiter plates used, the array of samples on the sample support can be finer than that corresponding to the microtiter plate. This can be achieved for example by a division of the microtiter plate microwell distances by integer numbers. In this way samples from several microtiter plates can be applied to a single sample support.

The basic microwell array of the original microtiter plate consists of 96 microwells in an array with distances of 9 mm arranged 8 rows and 12 columns. The form of the microtiter plate has been set as an industrial standard, although microtiter plates have been further developed to contain more microwells without changing their size. Modern implementations have 384, 864 or even 1536 microwells in grids of 4.5, 3.0 or 2.25 mm. These grid spacings can also be arranged for to the anchor fields on the purifying biosample supports. Regarding a droplet size of about 2 µl (easily and comfortably handled by the pipette robots), grid spacings with 4.5 or 3.0 mm and 384 or 864 anchor fields appear to be particularly favorable on the support. A droplet size of about 2 microliters should also be preferred since these droplets can be adequately and surely placed with automatic pipettes on the anchors, a situation which becomes more problematic with smaller droplet sizes.

When pipetting a drop of an aqueous biopolymer sample solution with a volume of about two microliters onto a hydrophilic anchor with a diameter of 400 microns, for example, a mushroom cap shaped drop forms with a diameter of about 1.5 to 2 millimeters. Under its own gravity it covers and wets a larger portion of the affinity adsorptive oleophilic ring (external diameter about 1.4 mm, for example). Such a covering is depicted in FIG. 1A. With an ideal embodiment of the carrier plate and the coating procedure, the lyophobic surroundings with even stronger hydrophobicity would not be wetted at all. While the droplet is drying, at which time vigorous fluid currents develop within it (which bring all molecules within the droplet many times into contact with the oleophilic surface of the affinity adsorbent), these molecules, due to their affinity towards oleophilic surfaces, will be bound by so-called hydrophobic binding, while the other, in general easily water soluble solution constituents will not be deposited until last on the surface, and then primarily on the hydrophilic anchors.

Before or after complete drying of the samples the sample carrier plate can be easily washed using washing fluid (for example with clean water for C18 coatings) in order to free it of all slightly water-soluble substances. By careful rinsing with a large excess of washing fluid there is usually no risk of any cross-contamination of the samples. If a guarantee against cross-contamination is required, individual rinsing of the individual anchor regions can be performed, for example by pipette rinsing, whereby the washing fluid is introduced and aspirated repeatedly. Drying then follows.

After drying, drops of organic solvents with small proportions of water and dissolved matrix substance are introduced as elution medium. The solvent containing small proportions of water and matrix substance immediately wets the affinity coating and releases the hydrophobically bound biopolymer molecules into the matrix solution. During drying the organic solvent evaporates first (e.g. methanol, acetone or acetonitrile); the increasing concentration of water and the rapidly decreasing volume allows the drop to shrink (often intermittently) more and more onto the anchor until the matrix substance crystallizes and the analyte molecules are incorporated there.

Alternatively the matrix substances may be loaded in the usual way to the hydrophilic anchor areas before the eluant is loaded. The eluant solvent then dissolves a lesser or larger part of the matrix substances, and the recrystallisation on the already existing residual crystal conglomerate is made easier.

Since the elution fluids are more easily capable to wet the affinity areas, much smaller volumes can be used for the drops; these can be deposited more easily onto the sample carrier plate from a pipette tip than can drops of pure water. Fluid quantities of about 200 to 500 nanoliters are sufficient, corresponding to droplet diameters of between 0.8 and 1 mm.

With a correct choice of water and matrix substance solution only a few biomolecules remain on the affinity coating. The biomolecules are incorporated to a large extent within the matrix crystals or at the boundary surfaces between the crystals.

Application of sample droplets at the start of coating proceeds conveniently when the multiple pipette is positioned at a distance of between 500 to 800 microns above the sample carrier plate. Approximately two microliters of sample solution are pipetted onto the sample support from each pipette tip of the multiple pipette; the diameter of free droplets is then about 1.6 millimeters. The pipette tips should be hydrophobic so that the application of the droplets is facilitated. The quantity of sample solution is usually sealed off in the pipette tip by a gas bubble so that no surplus solution is available in the channel of the pipette tip and the contact forces to the hydrophobic pipette tip are very small. In this way the drop can be reliably deposited on the sample carrier plate.

The drying droplets develop vigorous swirling fluid currents in their interior so that virtually all the biomolecules at some point come into contact with the affinity regions where they are affinely bound and therefore retained.

Washing can begin before the droplets are completely dried. In this way one can prevent impurities drying first so that they must then be resolubilized; this is sometimes a complicated process. Under certain circumstances, depending on the type of sample preparation and the associated impurities, one can postpone the washing until the droplets are completely dried.

Alternatively to the use of carrier plates in the size of microtiter plates, small metal or metallized strips can be used, equipped with only a smaller number of hydrophilic anchor areas which however are surrounded each by an affinity adsorption ring of different biospecificity. These strips then may be immersed completely into a solution of a mixture of biomolecules, e.g. diluted blood, to adsorb different groups of biosubstances on the different affinity regions and to analyze complete profiles of biosubstances like proteins. The strips may contain 3 to 10 different affinity areas, but larger numbers are also possible, depending on the analytical task. Washing then may be performed as described above.

After washing, the elution process is initiated on both types of sample carriers by the introduction of small quantities of eluant solution with dissolved matrix substance on each of the hydrophilic anchors, spreading out at the affinity regions and desorbing and resolving the biomolecules. The type of matrix substance depends on the analytical task; in principle hundreds of substances are known, even if only a handful of these are used frequently. These are all known to the mass spectrometry specialist. The matrix substances may be contained in the eluant solution, or may be deposited before elution on the hydrophilic anchors, and thus will be partly resolved by the eluant solution.

During drying, the droplets of the eluant fluid retract (in most cases intermittently) more and more from the affinity surfaces since the hydrophobia towards the affinity surface increases steadily due to preferential evaporation of the organic solvents. The last stage of drying leaves the crystal conglomerates with the largest part of the biomolecules exactly on the hydrophilic anchor regions as shown schematically in FIG. 1D. The lumpy MALDI samples are therefore positioned exactly as desired on their already known positions. Their size can be set in such a way that it corresponds to the focal surfaces of the laser beams. In addition they offer a high yield of analyte ions; they are thus ideally prepared for automatic analyses procedures.

Surprisingly, these monolithic lumps display a very good and (from lump to lump) reproducible ionization of the incorporated biomolecules, at least as good as the most favorable locations arduously sought for with the previously described type of preparation. Adduct formation with alkali ions is much lower, and can even be completely suppressed by ion exchange materials. The analyte molecules are probably embedded in a location which is highly favorable for the desorption and ionization process, at the boundaries between the grains of the microcrystalline structure.

The droplets can of course also be applied manually; there are many possible ways to use the sample supports described here, as any expert in this area shall become aware of after reading this report.

From the nature and course of the cleaning and drying processes it follows that certain compositions of sample solutions should be avoided. Supplementation with surfactants or detergents is harmful since a wetting of the hydrophibic or even lyophobic surfaces can occur under such conditions. It should also be apparent to any expert after reading this report how he/she should carry out sample preparation and pipetting procedures in order to avoid any erroneous application of samples.

Both hydrophobic and hydrophilic surfaces can change their wetting qualities during long term storage in ambient air due to the deposition of air contaminants. It is therefore advisable to store the sample supports in a vacuum or under an atmosphere of a clean protective gas.

The invention claimed is:

1. A method for loading purified biomolecules from largely unpurified analytical biosample solutions to a sample support plate for a subsequent mass spectroscopic analysis with ionization by matrix-assisted laser desorption and ionization (MALDI), comprising the following steps
   (a) providing a sample support plate with three separate surface areas, including affinity adsorption surface areas each adjacent to a hydrophilic anchor surface area on an otherwise strongly hydrophobic plate surface, wherein the affinity adsorption areas are less hydrophobic than a lyophobic plate surface, but more hydrophobic than the hydrophilic anchor areas,
   (b) exposing the affinity adsorption areas to analytical sample solutions containing the biomolecules, thereby adsorbing the biomolecules to be analyzed,
   (c) washing the sample support plate comprising the adsorbed biomolecules with a solution that does not elute the adsorbed biomolecules,
   (d) desorbing the adsorbed biomolecules by an eluant solution which also contains matrix substance, and
   (e) drying the eluant solution, thereby forming matrix crystals containing desorbed biomolecules on the hydrophilic anchor areas.

2. A method according to claim 1, wherein in step (a) a sample support plate with adsorption areas of different biospecificities is provided, and wherein, in the exposing step (b), the sample support plate is completely immersed in the analytical sample solution to adsorb different types of biomolecules on different adsorption areas.

3. A method according to claim 1, wherein in step (b) the affinity adsorption areas are exposed to the analytical sample solution by application of drops of the analytical sample solution larger in size than the hydrophilic anchor areas, so that the drops on the sample support plate overlap with the affinity adsorption areas.

4. A method according to claim 1, wherein the eluant solution in step (d) does not contain a matrix substance, but a solution with a matrix substance is loaded onto the hydrophilic anchor areas between steps (c) and (d), and dried and the dried matrix substance is partially re-dissolved in step (d) by the eluant solution.

5. A method according to claim 1, wherein the affinity adsorption areas on the sample support plates provided in step (a) form rings around the hydrophilic anchor areas.

6. A method according to claim 1, wherein the eluant solution applied in step (d) is an organic solvent with a small part of water.

* * * * *